United States Patent
Ramin et al.

(10) Patent No.: US 11,478,293 B2
(45) Date of Patent: Oct. 25, 2022

(54) ELECTROSURGICAL GENERATOR

(71) Applicant: OLYMPUS WINTER & IBE GMBH, Hamburg (DE)

(72) Inventors: Daniel Ramin, Nuthetal (DE); Thomas Fähsing, Blankenburg (DE); Stefan Schiddel, Stahnsdorf (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 303 days.

(21) Appl. No.: 16/617,401

(22) PCT Filed: Jun. 6, 2018

(86) PCT No.: PCT/EP2018/064929
§ 371 (c)(1),
(2) Date: Nov. 26, 2019

(87) PCT Pub. No.: WO2018/224564
PCT Pub. Date: Dec. 13, 2018

(65) Prior Publication Data
US 2020/0085488 A1    Mar. 19, 2020

(30) Foreign Application Priority Data
Jun. 8, 2017 (DE) .......................... 102017112684.8

(51) Int. Cl.
*A61B 18/12* (2006.01)
*A61B 18/00* (2006.01)

(52) U.S. Cl.
CPC .. *A61B 18/1206* (2013.01); *A61B 2018/0063* (2013.01); *A61B 2018/00178* (2013.01);
(Continued)

(58) Field of Classification Search
CPC .. A61B 2018/00869; A61B 2018/1266; H02H 3/302; H02H 3/343; H02H 3/353; H02H 3/382
See application file for complete search history.

(56) References Cited

U.S. PATENT DOCUMENTS

2006/0126240 A1 * 6/2006 Unger .................... H02J 9/062
                                                                                       361/62
2010/0217259 A1    8/2010 Strauss
(Continued)

FOREIGN PATENT DOCUMENTS

CN      104224309 A    12/2014
CN      104578854 A    4/2015
(Continued)

OTHER PUBLICATIONS

Mar. 19, 2018 Office Action issued in German Patent Application No. 10 2017 112 684.8.
(Continued)

*Primary Examiner* — Joanne M Hoffman
*Assistant Examiner* — Sean W Collins
(74) *Attorney, Agent, or Firm* — Oliff PLC

(57) ABSTRACT

An electrosurgical generator having connectors for an electrosurgical instrument including a high-voltage generator electrically connected to the connectors and produces a high-frequency alternating current in its activated state and output said high-frequency alternating current via the connectors. The electrosurgical generator has an effective power determination unit including a phase shift determination unit that supplies an output signal representing a phase shift between the current and the voltage of an alternating current output during operation. The phase shift determination unit produces a pulsed DC voltage signal, in which the pulse width reflects a time difference between the zero crossings of the current and the voltage—and consequently the phase
(Continued)

Figure 1:
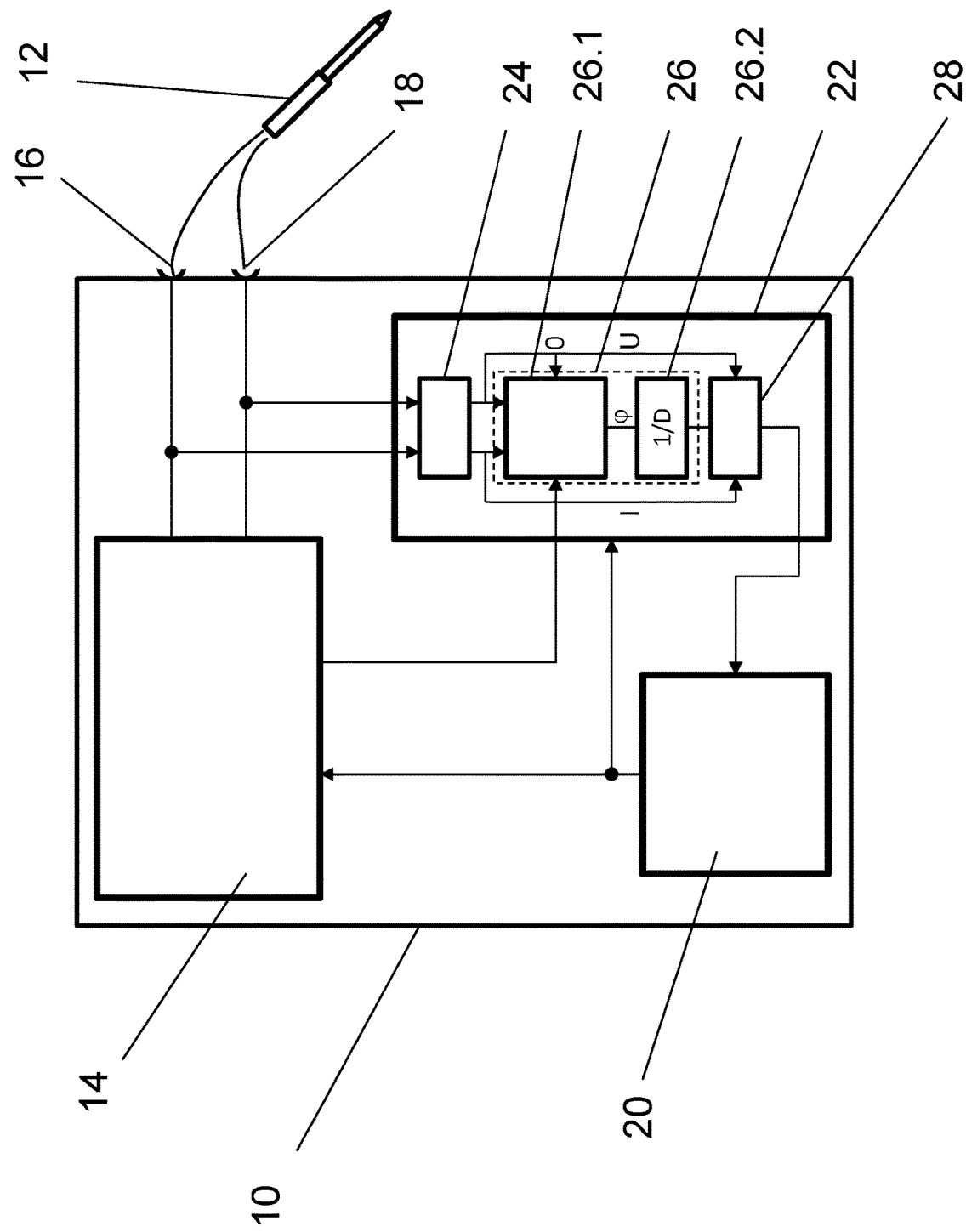

shift—and to process the pulsed DC voltage signal by way of a low-pass filter to form a low-pass filter output signal, the magnitude of which depends on the pulse width of the pulses of the pulsed DC voltage signal.

9 Claims, 7 Drawing Sheets

(52) U.S. Cl.
CPC ............... *A61B 2018/00577* (2013.01); *A61B 2018/00589* (2013.01); *A61B 2018/00595* (2013.01); *A61B 2018/00827* (2013.01); *A61B 2018/00869* (2013.01); *A61B 2018/00892* (2013.01); *A61B 2018/1266* (2013.01)

(56) References Cited

U.S. PATENT DOCUMENTS

| | | | |
|---|---|---|---|
| 2012/0095461 A1 | 4/2012 | Herscher et al. | |
| 2012/0206177 A1* | 8/2012 | Colinet | H03L 7/087 |
| | | | 327/156 |
| 2015/0196344 A1 | 7/2015 | Wham et al. | |
| 2015/0265347 A1* | 9/2015 | Yates | A61B 18/1445 |
| | | | 606/50 |
| 2016/0000495 A1* | 1/2016 | Elliott | A61B 18/1233 |
| | | | 606/34 |
| 2018/0042660 A1 | 2/2018 | Assmus et al. | |

FOREIGN PATENT DOCUMENTS

| | | | |
|---|---|---|---|
| DE | 10 2007 051 097 A1 | 4/2009 | |
| DE | 10 2010 040 824 A1 | 3/2012 | |
| DE | 10 2011 078 452 A1 | 1/2013 | |
| DE | 10 2015 204 127 A1 | 9/2016 | |
| EP | 2 100 566 B1 | 7/2013 | |
| EP | 2 200 527 B1 | 11/2014 | |
| GB | 2027295 A * | 2/1980 | ........... H03D 13/004 |
| JP | 2011-509100 A | 3/2011 | |
| JP | 2013-523318 A | 6/2013 | |
| WO | 98/44855 A1 | 10/1998 | |

OTHER PUBLICATIONS

Sep. 14, 2018 Search Report issued in International Patent Application No. PCT/EP2018/064929.
Sep. 14, 2018 Written Opinion of the International Searching Authority issued in International Patent Application No. PCT/EP2018/064929.
Mar. 16, 2022 Office Action issued in Chinese Patent Application No. 201880029442.5.

\* cited by examiner

ELECTROSURGICAL GENERATOR

The invention relates to an electrosurgical generator having connectors for connecting an electrosurgical instrument.

The electrosurgical generator comprises a high-voltage generator, which is electrically connected to the connectors for the electrosurgical instrument and which is designed to produce a high-frequency alternating current in its activated state and output said high-frequency alternating current via the connectors. The electrosurgical generator has an effective power determination unit that is able to detect a phase shift between the current and the voltage of an high-frequency alternating current output by the electrosurgical generator during operation, in order to determine the effective power output by the electrosurgical generator during use via a connected electrosurgical instrument.

Such electrosurgical generators are, inter alia, used in connection with electrosurgical instruments by means of which body tissue can be coagulated or ablated. It is, for example, a known procedure to conduct a high-frequency alternating current through the adjoining body tissue via electrodes of the electrosurgical instrument that, during use, are in contact with body tissue, in order to thus heat the body tissue such that it is denatured. Tumors, for example, can be treated in this manner, or tissue parts can be cauterized or fused together for other purposes.

Known electrosurgical generators have an effective power determination unit that is designed to produce an output signal representing a phase shift between the current and the voltage of an alternating current output by the electrosurgical generator during operation. The effective power determination unit comprises a phase shift determination unit with a low-pass filter and is designed to determine a time difference between the zero crossings of the current and the voltage and to produce an output signal the magnitude of which reflects this time difference. The phase shift determination unit preferably comprises a zero crossing detector that produces a detector output signal, the pulse width of which corresponds precisely to the duration of the phase shift between the current and the voltage. Subsequently, the low-pass filter converts this detector output signal into a DC voltage, the magnitude of which represents the phase shift. If the phase shift is known due to the aforementioned procedure, the effective power can be determined in a, as such, known manner as the product of the root mean square values of current and voltage and the cosine of the phase shift angle.

It has turned out that, in practice, such known effective power determination units occasionally provide incorrect values.

It is therefore the underlying object of the invention to create an improved electrosurgical generator that reliably determines the effective power that is output by it.

Pursuant to the invention, an electrosurgical generator of the above described type is to this end provided with a switch unit that is arranged and designed such that a detector output signal will only be supplied if the high-voltage generator is in its activated state, but not if the high-voltage generator is switched off and the power that might be output via the connectors is due to residual oscillations.

In the simplest case, for example, the effective power determination unit is immediately switched off when the high-voltage generator of the electrosurgical generator is switched off as well. It is, however, preferable that the switch unit is arranged between an output of the phase shift determination unit and an input of the low-pass filter so that the input of the low-pass filter receives a zero signal as soon as the high-voltage generator is switched off.

The invention incorporates the realization that especially residual oscillations and attenuating oscillations after the high-voltage generator has been switched off impact the effective power determination units of the above described type in such a way that they provide incorrect output values. Therefore, it is advantageous if, immediately after the high-voltage generator has been switched off, the effective power determination unit no longer receives a, as the case may be, incorrect detector output signal produced by the phase shift determination unit.

The switch unit leads to a decoupling of the residual oscillations on the hardware side, so that only signals that are detected when an input control signal (the generator on signal) is present will influence the determination of the signal representing the effective power of the output alternating current.

In a particularly advantageous embodiment, the switch unit is designed as an AND gate with two inputs and one output, wherein one of the inputs is connected to an output of the phase shift determination unit and wherein, during the activated state of the high-voltage generator, the other input receives a "generator on" signal, and wherein the output of the switch unit is connected to the low-pass filter. In other words, an AND gate is connected between the output of the phase shift determination unit and the input of the low-pass filter, which will only pass on the detector output signal of the phase shift determination unit to the input of the low-pass filter if a "generator on" signal is present at the second input of the AND gate. The "generator on" signal is a signal that is only present when the high-voltage generator is being operated and is not switched off. When the high-voltage generator is switched off, the "generator on" signal is a zero signal and the AND gate locks so that the detector output signal is not able to reach the input of the low-pass filter.

In other preferred embodiments, the phase shift determination unit has two comparators. Of these, a first comparator is designed and arranged to compare a voltage signal with a zero signal, and to produce an output signal if an instantaneous value of the voltage is greater than the zero signal. The second comparator is designed and arranged to compare a zero signal with a current signal, and to produce an output signal if the zero signal is greater than the instantaneous value of the current, i.e. if the instantaneous value of the current is negative. In other words, the first comparator supplies an output signal when the instantaneous value of the voltage is positive, i.e. greater than zero, while the second comparator supplies an output signal when the current value is negative, i.e. less than zero. Thus, an output signal will be supplied by both comparators only if the instantaneous value of the voltage has passed through a zero crossing from positive to negative and if, at the same time, the instantaneous value of the current has not yet passed through a zero crossing from positive to negative.

Of course, the comparators may also be switched in precisely the opposite way so that the first comparator supplies an output signal when the instantaneous value of the voltage is less than zero, while the second comparator only supplies an output signal when the instantaneous value of the current is greater than zero.

In this preferred embodiment, the outputs of the two comparators are connected to each other such that the two comparators will only output a combined output signal as the detector output signal with a magnitude exceeding a threshold value, if the instantaneous value of the voltage is positive—i.e. greater than the zero signal—and if, at the same time, the instantaneous value of the current is negative—i.e. less than zero. In the opposite case, which is an equally possible option, the outputs of the two comparators are connected to each other such that the two comparators will only output a combined output signal as the detector output signal with a magnitude exceeding a threshold value, if the instantaneous value of the current is positive—i.e. greater than the zero signal—and if, at the same time, the instantaneous value of the voltage is negative—i.e. less than zero.

Other preferred embodiments of the electrosurgical generator are characterized in that the high-voltage generator is designed to output the high-frequency alternating current in its activated state via the connectors, pulsed with a duty cycle. In other words, no continuous alternating current is output via the connectors, but the alternating current is interrupted regularly, i.e. it is pulsed. This can, for example, be achieved by means of a phase-fired controller, so that the maximum effective power does not have to be output permanently and the effective power to be output can also be set to lower values in a controlled manner.

One problem in connection with such a, per se, desirable electrosurgical generator is that, in case of a pulsed alternating current, it is not possible to reliably determine the effective power, since the effective power determination unit is impacted by the pulsing of the output alternating current. In this case, it is therefore required that the effective power determination unit is designed to multiply the DC voltage produced by the low-pass filter by a correction value that depends on the duty cycle of the output alternating current, and to output a thus corrected DC voltage as a signal representing the phase shift.

Of course, such a correction of the DC voltage produced by the low-pass filter as the signal representing the phase shift can also be provided for independently by a switch unit pursuant to the invention and thus constitutes an inventive idea that may also be realized independently. In other words, it is possible to provide a correction of the output DC voltage of the low-pass filter dependent on the duty cycle for an electrosurgical generator of the initially mentioned type without said electrosurgical generator having means such as the above described switch unit that prevent that a detector output signal is passed on to the low-pass filter when the high-voltage generator is switched off.

The combination of both measures—i.e. a switch unit for blocking the low-pass filter input when the high-voltage generator is switched off and the correction of the DC voltage produced by the low-pass filter dependent on the duty cycle—leads to a significantly more reliable determination of the effective power.

The correction value by which the DC voltage produced by the low-pass filter is multiplied preferably corresponds to the reciprocal of the duty cycle.

Preferably, the electrosurgical generator has a control unit that is connected to the high-voltage generator and controls it. The control unit is preferably connected to the effective power determination unit and designed to receive an output signal from the effective power determination unit, which depends on the phase shift between the current and the voltage of the high-frequency alternating current output by the electrosurgical generator during operation.

Preferably, the control unit is further designed to output a signal representing the duty cycle (D) to the control circuit.

Figure 2:
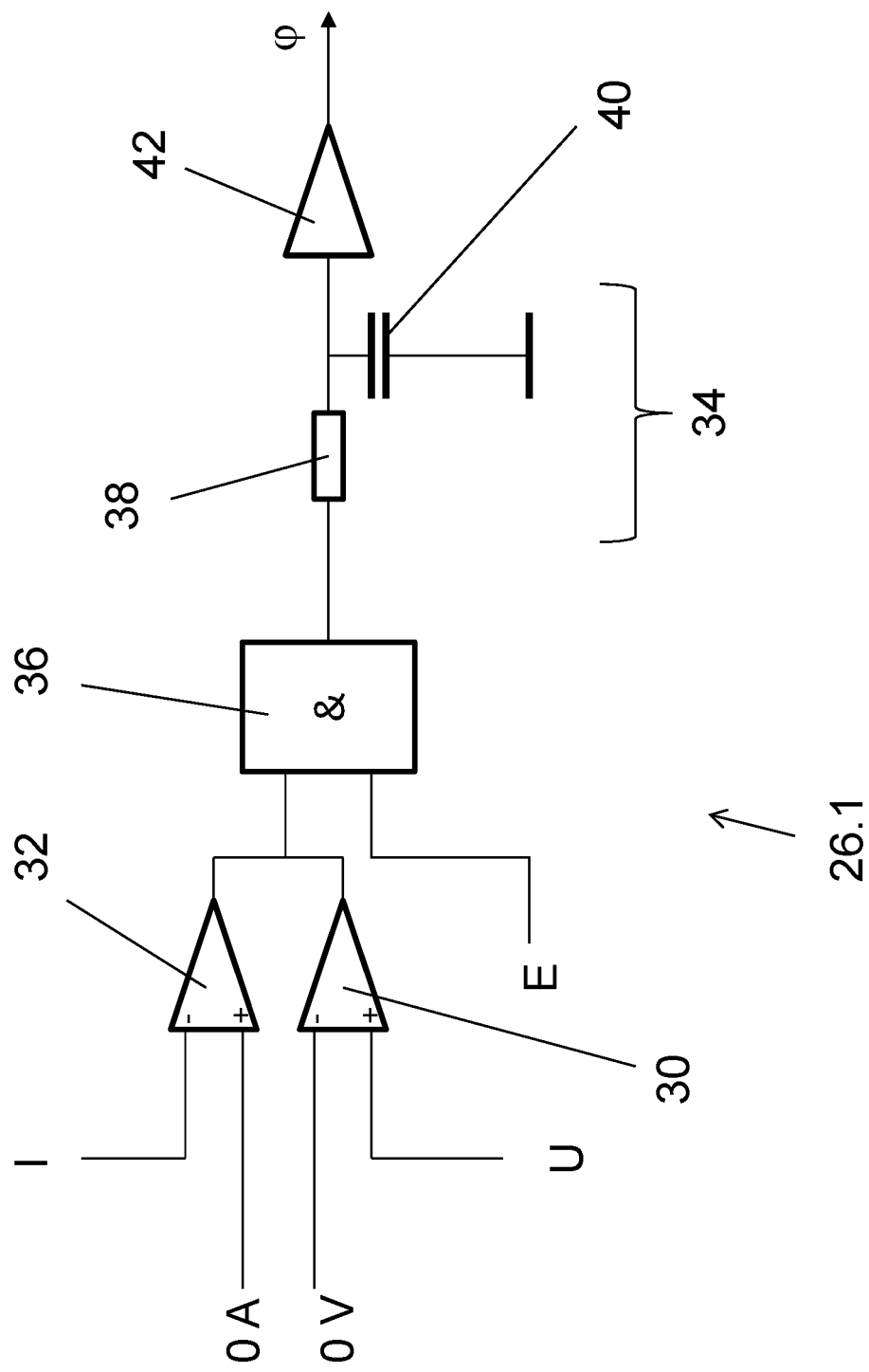
Figure 3:
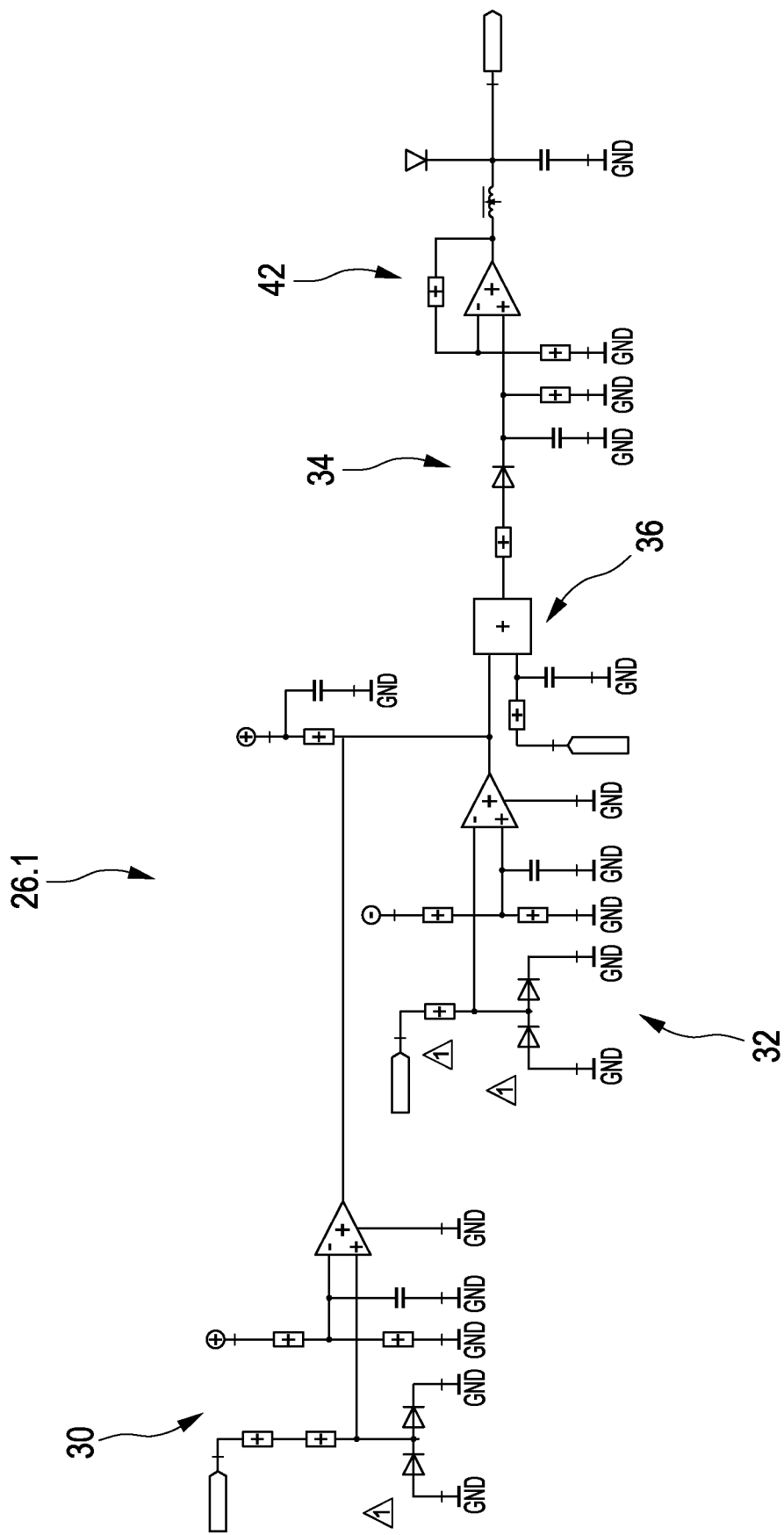

In the following, the invention shall be explained in more detail based on exemplary embodiments with reference to the accompanying figures. The figures show the following:

FIG. 1: a schematic block diagram of an electrosurgical generator with a connected electrosurgical instrument;

FIG. 2: a schematic block diagram of an effective power determination unit for an electrosurgical generator pursuant to FIG. 1;

FIG. 3: an exemplary circuit diagram of an effective power determination unit pursuant to the invention;

FIGS. 4a and 4b: drawings explaining the operating principle of the phase shift determination unit;

FIGS. 5a to c: drawings of signals impacted by the residual oscillations of the high-voltage generator to explain the technical problem the invention is based on;

FIGS. 6a to c: drawings of the signals in the form in which they occur without a switch unit pursuant to the invention; and FIGS. 7a to c: drawings of the signals in the form in which they occur with a switch unit pursuant to the invention.

FIG. 1 shows a schematic block diagram of an electrosurgical generator 10 with a connected electrosurgical instrument 12.

The electrosurgical generator comprises a high-voltage generator 14, which, via its outputs 16 and 18, supplies high-frequency alternating voltage to the electrosurgical instrument 12. Said voltage is released into body tissue via the electrosurgical instrument 12.

For the output of the electrosurgical instrument 12 to be able to be controlled, the high-frequency alternating voltage output by the high-voltage generator 14 is modulated, i.e. it is pulsed with a duty cycle, such that the high-voltage generator 14 is switched off and on in accordance with the duty cycle. A control unit 20 controls at what times the high-voltage generator 14 is switched on and off.

The effective power actually released into the body tissue by the high-voltage generator 14 via the electrosurgical instrument 12 depends inter alia on the impedance of the body tissue. The impedance of the body tissue and other factors lead to a phase shift between the voltage and the current, i.e. between the high-frequency alternating voltage output by the high-voltage generator 14 and the pertaining high-frequency alternating current. In order to be able to determine the output effective power, the electrosurgical generator 10 must therefore determine a value representing the respective current phase shift.

For this purpose, an effective power determination unit 22 is designed to detect a phase shift between the current and the voltage of a high-frequency alternating current output during operation. To this end, a current and voltage measuring unit 24 is electrically connected to the outputs 16 and 18 of the high-voltage generator 14 and measures on the one hand the respective instantaneous voltage and, on the other, the respective instantaneous current and passes on the output signals representing the instantaneous value of the current and/or the voltage to a phase shift determination unit 26 with a downstream low-pass filter, which is not shown separately.

Since the instantaneous values of the current and the voltage vary, the input signals of the phase shift determination unit represent on the one hand the chronological development of the voltage output by the high-voltage generator 14, and, on the other, the chronological development of the current output by the high-voltage generator 14. The input signal representing the chronological development of the voltage and the input signal representing the chronological development of the current are each approximately periodic and phase-shifted in relation to each other.

The phase shift determination unit 26 is designed to respectively detect either positive or negative zero crossings of the current and/or the voltage curve, and, after having detected the first zero crossing of the current and/or the voltage curve, to output an output signal with a positive magnitude value until a corresponding positive or negative zero crossing of the pertaining phase-shifted current and/or voltage curve is detected. Thus, an intermediate output signal produced by the phase shift determination unit is a pulsed DC voltage signal, the respective pulse width of which corresponds, from a chronological point of view, to the phase shift between the current and the voltage (or vice versa). When this pulsed DC voltage signal is supplied to a low-pass filter, the result is a smoothed DC voltage signal, the magnitude of which depends on the phase shift φ. The magnitude is greater when the phase shift is greater, and the magnitude of the smoothed (low-pass filtered) output signal is smaller when the phase shift is smaller. Thus, the smoothed, low-pass filtered output signal of the phase shift determination unit 26 represents the phase shift between the current and the voltage, and can be used for the determination of the effective power output by the high-voltage generator 14. For this purpose, the determination unit 28 is provided, which determines the root mean square values of the current and the voltage and determines the effective power based on them and on the phase shift.

Since the smoothed average value representing the phase shift also depends on the duty cycle with which the high-frequency alternating voltage output by the high-voltage generator 14 is modulated, the effective power determination unit is also supplied with a value representing the duty cycle D. To this end, the effective power determination unit 22 is connected to the control unit 20. In turn, the value for the actually output effective power determined by the effective power determination unit 22 is supplied to the control unit 20, making it possible to control the power.

The effective power determination unit 22 can then determine the effective power as follows:

$$P = U_{eff} \cdot I_{eff} \cdot \cos\left(\varphi \cdot \frac{1}{D}\right)$$

Thus, the phase shift determination unit 26 comprises a part 26.1 that establishes the moving average of the pulse sequence 56 that depends on the phase shift, and a second part 26.2 by means of which this smoothed average is corrected. The correction, i.e. the implementation of the second part 26.2 and the calculation of the cosine and the effective power, may be implemented in the software and be executed in the control unit 20. This means that the components 26.2 and 28 may also be software-implemented as part of the control unit 20.

One possible implementation of the first part 26.1 of the phase shift determination unit 26 is realized as a circuit and shown in FIG. 2.

A first comparator 30 compares a respective instantaneous value of the voltage with a 0 volt signal. A second comparator 32 compares the respective instantaneous value of the current with a 0 ampere signal. As long as the instantaneous value of the voltage is greater than 0 volt, the first comparator 30 will output a positive output signal. At the second comparator 32, the respective instantaneous value of the current is supplied to the inverted input, while the 0 ampere signal is supplied to the non-inverted input of the second comparator 32. Accordingly, the second comparator 32 will output a negative output signal as long as the instantaneous value of the current is greater than 0 ampere.

Thus, as long as both the instantaneous value of the voltage and the instantaneous value of the current are greater than the respective zero value, the output values of the two comparators 30 and 32 cancel each other out, so that, added together, the two comparators 30 and 32 output a zero signal. Only once the instantaneous value of the current drops below 0 ampere, i.e. when the chronological development of the instantaneous value of the current makes a zero crossing in the negative direction, will the combined output signal of the two comparators 30 and 32 become positive, namely until, a short time later, the chronological development of the instantaneous value of the voltage also makes a zero crossing from positive to negative. In the moment in which the instantaneous value of the voltage also drops below zero volt and the instantaneous value of both the current and the voltage are respectively less than the corresponding zero value, the output signals of the comparators 30 and 32 will once again cancel each other out. Accordingly, the combined output value of the two comparators 30 and 32 will only be different for as long as the instantaneous value of the voltage is already less than zero volt, while the instantaneous value of the current is still greater than zero ampere. This means that the combined output signal of the two comparators 30 and 32 is a pulsed DC voltage signal, the pulse width of which corresponds exactly to the duration of the phase shift between the current and the voltage.

Thus, the two comparators 30 and 32 form a zero crossing detector, the output signal of which is the pulsed DC voltage signal.

Said pulsed DC voltage signal is supplied to a low-pass filter 34, which smoothes the pulsed DC voltage signal. The magnitude of the low-pass filtered, smoothed DC voltage signal, i.e. the magnitude of the output signal of the low-pass filter 34, depends on the pulse width of the pulses of the pulsed, combined output signal of the comparators 30 and 32. The greater the phase shift, the greater the pulse width of the pulsed DC voltage signal will be, and the greater the magnitude of the low-passed filtered, smoothed output signal of the low-pass filter 34 will be. If the phase shift is zero, the pulse width of the pulsed DC voltage signal, as the combined output signal of the two comparators 30 and 32, will also be zero, and the magnitude of the low-pass filtered, smoothed output signal of the low-pass filter 34 will be zero as well.

Since the effective power output by the high-voltage generator 14 does not only depend on the phase shift between the current and the voltage, but also on the duty cycle with which the high-frequency alternating voltage (and/or the high-frequency alternating current) is modulated, the low-pass filtered, smoothed output signal of the low-pass filter 34 does not only reflect the phase shift, but also depends on the duty cycle with which the high-frequency output voltage of the high-voltage generator 14 is modulated. In order to actually obtain a value that only represents the phase shift, one has to multiply the smoothed, low-pass filtered output signal of the low-pass filter 34 by the reciprocal of the duty cycle D (i.e. by 1/D). This can be performed in the control unit 20.

In practice, this as well does not lead to an output value of the low-pass filter 34 which only represents the phase shift, since the residual oscillations of the high-voltage generator 14 after it has been switched off have the result that the phase shift determination unit 26 still detects zero crossings and the combined output signal of the comparators 30 and 32 accordingly still shows pulses of the pulsed DC voltage when the high-voltage generator 14 is actually already switched off. These residual oscillations artificially increase the output value of the low-pass filter 34 and suggest a greater phase shift than actually present.

For the solution of this problem, a switch unit 36 in the form of an AND gate 36 is provided, which only passes on the combined output signal of the comparators 30 and 32 to the low-pass filter 34 when the high-voltage generator 14 is actually switched on. To this end, the AND gate 36 is supplied at one input with the combined output signal of the comparators 30 and 32, i.e. with the pulsed DC voltage, while the other input signal of the AND gate 36 is supplied with the "on" signal for the high-voltage generator 14. This means that the pulses of the pulsed DC voltage can, as a combined output signal of the comparators 30 and 32, reach the output of the AND gate 36 and thus the input of the low-pass filter 34 only if the "on" signal is positive, i.e. if the high-voltage generator 14 is switched on. Thus, the low-pass filter 34 only receives the combined output signal of the comparators 30 and 32 as long as the high-voltage generator 14 is actually switched on, while potential attenuating oscillations are ignored.

As can be seen in FIG. 2, the two comparators 30 and 32 are respectively realized by means of correspondingly switched operational amplifiers. The switch unit 36 is, as already explained, designed as an AND gate 36. The low-pass filter 34 comprises in a, as such, known manner an input resistance 38 and a capacitor 40 that is switched to ground as well as a downstream operational amplifier 42.

FIG. 3 shows an example of a specific embodiment of the comparators 30, 32, of the AND gate 36 and the low-pass filter 34 with downstream operational amplifier.

FIGS. 4a and 4b illustrate how the phase shift determination unit 26 works.

Figure 4:
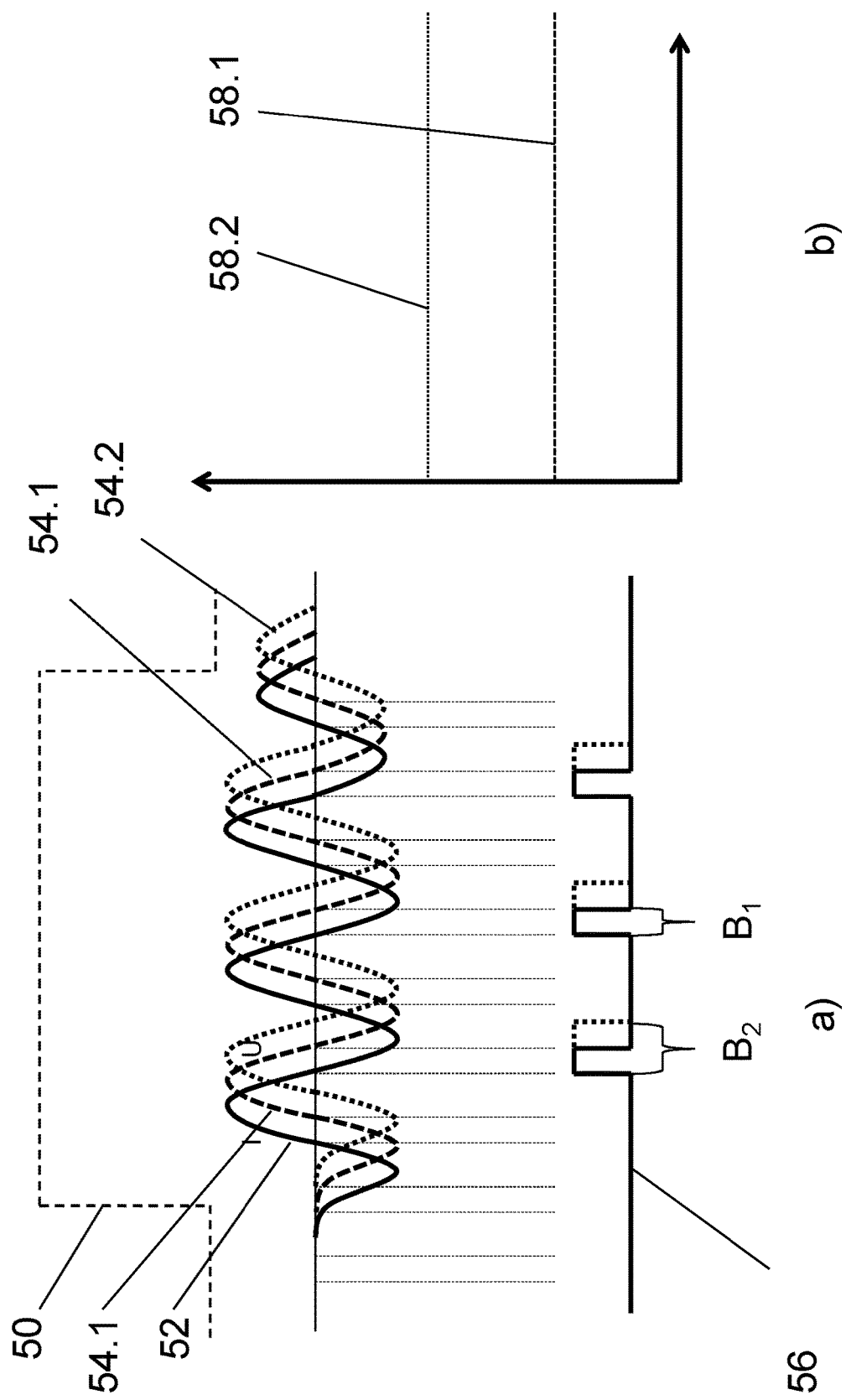

A dashed line at the top of FIG. 4a shows the development of the turn-on signal 50 for the high-voltage generator 14. The solid line represents the chronological development of the current 52, while the dashed line represents the chronological development of the voltage 54.1 and/or 54.2. For the sake of simplicity, the current and the voltage are shown with the same amplitude; however, in practice, the amplitudes may vary, depending also on the scaling. FIG. 4a shows two different voltage curves 54.1 and 54.2, which represent two different phase shifts between the current and the voltage. In the case of the voltage curve 54.1, the phase shift between the current and the voltage is smaller than in the case of the voltage curve 54.2. The line at the bottom of FIG. 4 represents the combined output signal 56 of the comparators 30 and 32. As can be seen, the combined output signal 56 is a pulsed DC voltage signal, the pulse width B of which corresponds exactly to the duration of the phase shift between the current and the voltage. In the case of the smaller phase shift between the current curve 52 and the voltage curve 54.1, the pulses of the pulsed DC voltage signal 56 have a duration B1. In the case of a larger phase shift, the pulse duration is longer and assumes the value B2.

When the pulsed DC voltage represented by the lower line in FIG. 4a is low-pass filtered and thus smoothed, the result is a DC voltage with a magnitude that depends on the duration, i.e. the pulse width of the pulses of the pulsed DC voltage signal 56. This is shown in FIG. 4b. The dashed bottom line 58.1 represents a low-pass filtered DC voltage as obtained through the low-pass filtering of the pulsed DC voltage with the pulse width B1, while the dotted line 58.2 on top shows a smoothed DC voltage with a greater magnitude as obtained through the low-pass filtering of the pulsed DC voltage 56 with voltage pulses of a duration B2.

For the sake of simplicity, FIG. 4a shows by way of extract, an approximately steady state while the high-voltage generator 14 is switched on.

Figure 5:
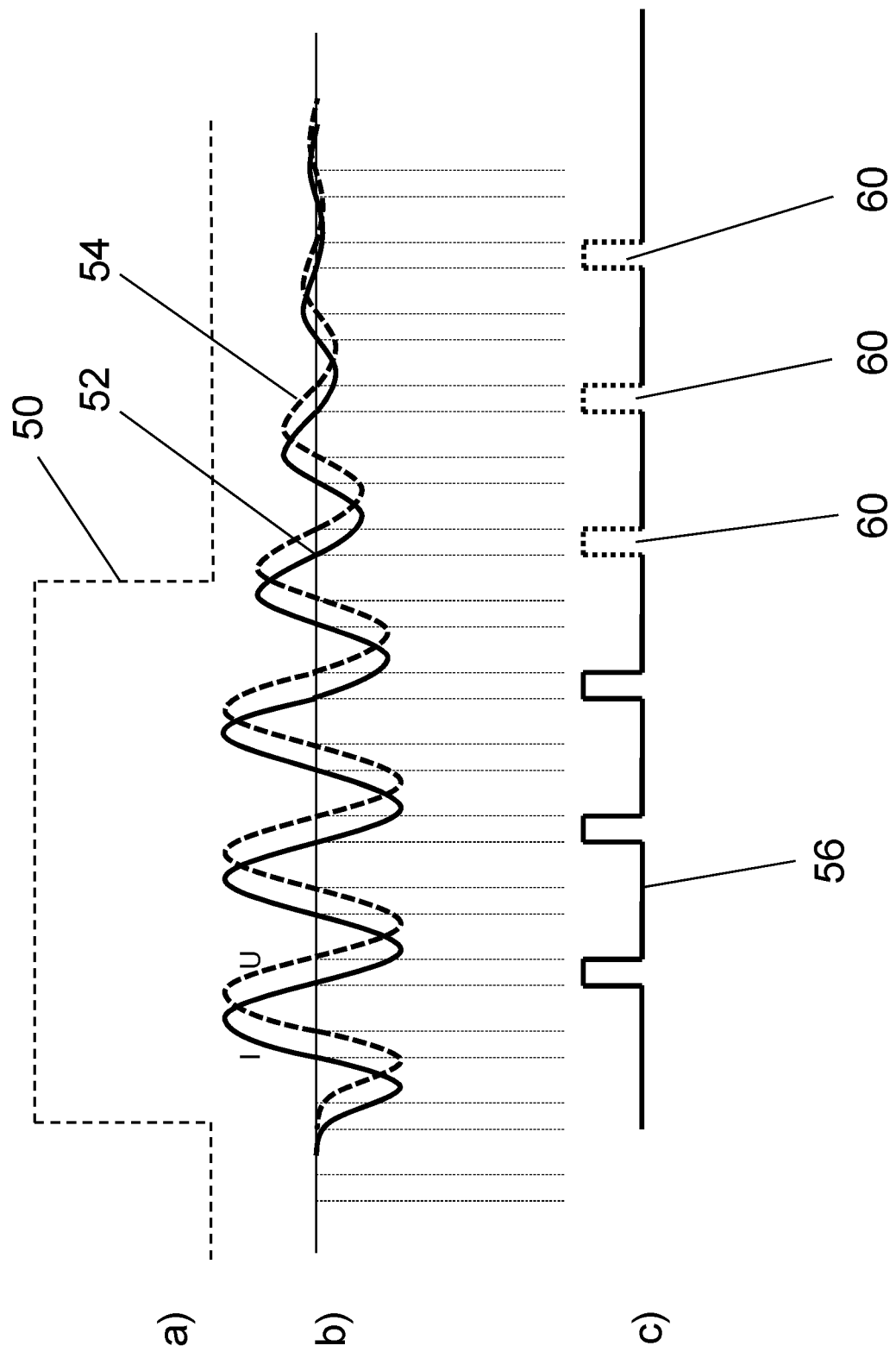

FIG. 5 shows that, after the high voltage generator 14 has been switched off—which can be inferred from the drop of the turn-on signal 50; cf. FIG. 5a)—residual oscillations occur in the current curve 52 and in the voltage curve 54 (cf. FIG. 5b), which lead to additional detected zero crossings and, therefore, to the pulses 60 in the curve representing the pulsed DC voltage signal 56 (cf. FIG. 5c). If the pulsed DC voltage signal 56 is low-pass filtered for a longer period of time, the magnitude of the resulting smoothed DC voltage signals also depends on the pulses 60 caused by the residual oscillations. If those pulses were not present, the magnitude of the low-passed filtered, smoothed DC voltage signal would be smaller. If the magnitude of the smoothed DC voltage signal is multiplied by the reciprocal of the duty cycle for the turn-on signal 50, the result is—due to the pulses 60 caused by the residual oscillations—magnitude, and thus an output signal of the phase shift determination unit that does not reflect the phase shift between the current and the voltage correctly, but is distorted due to the pulses 60 caused by the residual oscillations.

In order to counteract this, the switch unit 36, namely the AND gate 36, which de facto suppresses the pulses 60 caused by the residual oscillations, is provided in the phase shift determination unit 36.

Figure 6:
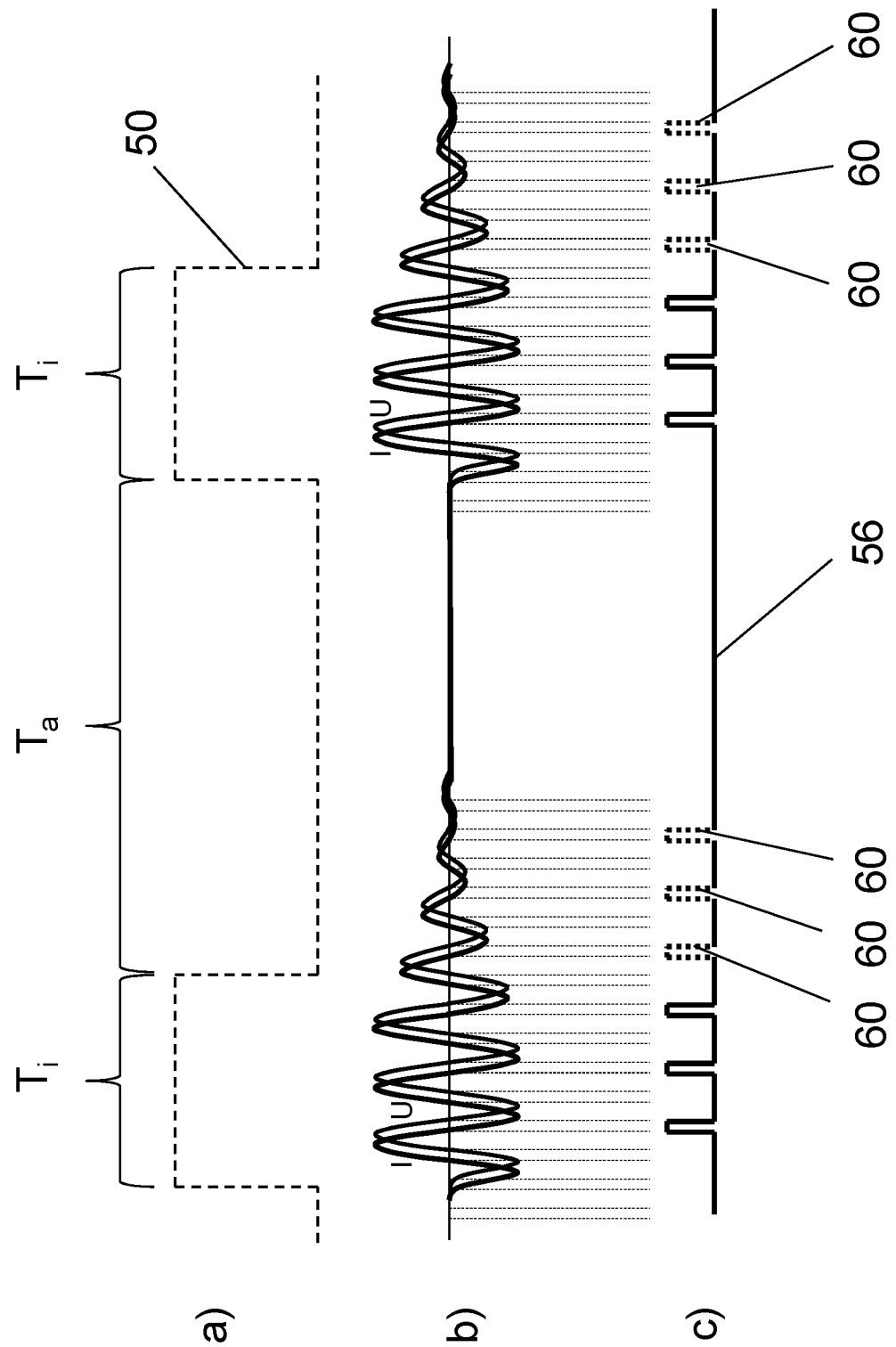
Figure 7:
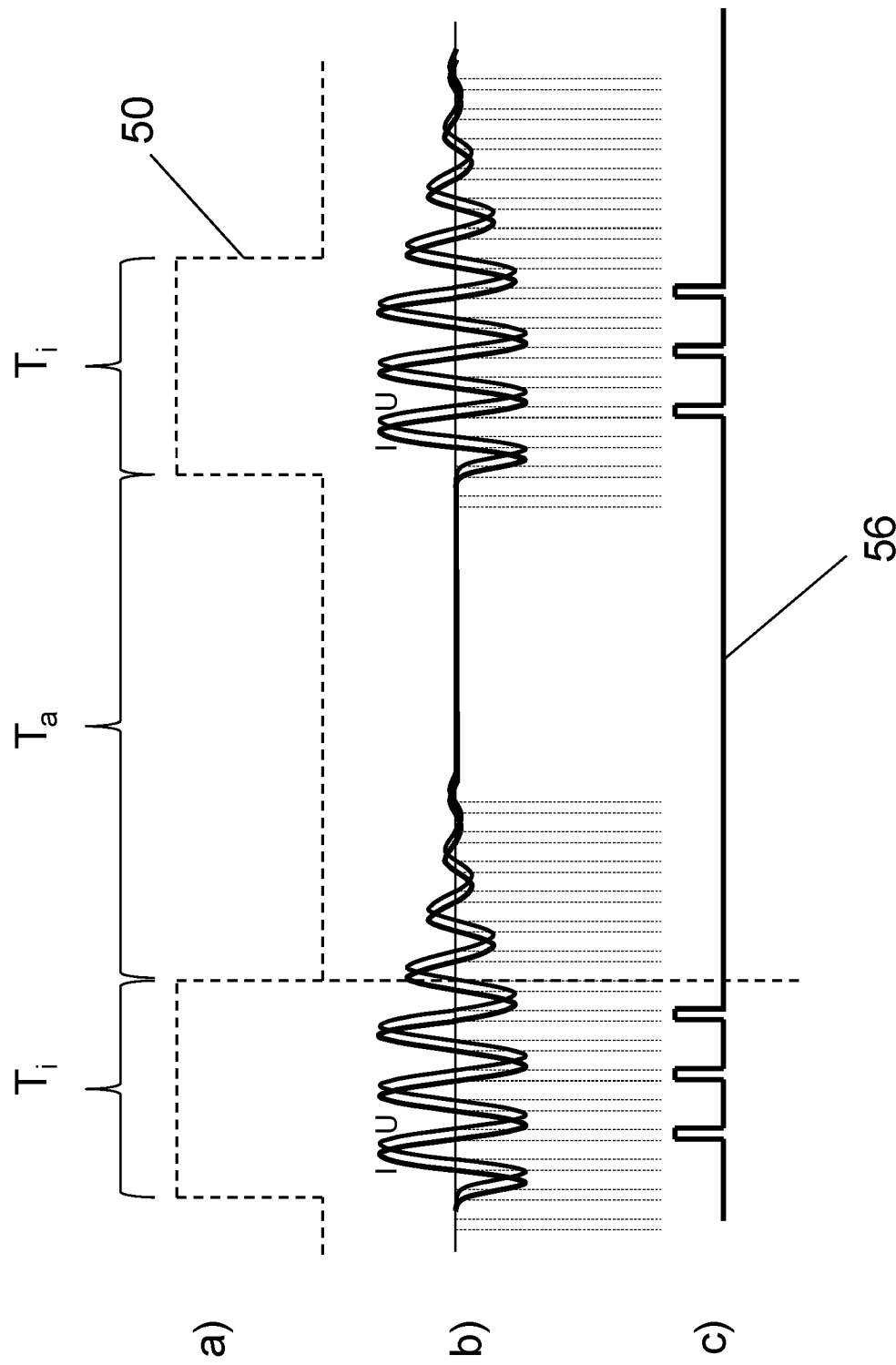

This is explained in FIGS. 6 and 7. FIG. 6 shows the development of the pulsed DC voltage 56 that occurs when no switch unit 36 is provided.

FIG. 7 shows that the pulses 60 are suppressed by the switch unit 36. If the pulsed DC voltage signal 56 shown in the bottom line of FIG. 7 is low-pass filtered and if the low-pass filtered value is multiplied by the reciprocal of the duty cycle of the turn-on signal 50, the resulting magnitude reflects the phase shift between the current curve 52 and the voltage curve 54 fairly accurately.

The duty cycle of the turn-on signal 50 is $$D = \frac{T_i}{T_a}.$$

The reciprocal of the duty cycle is thus $$\frac{1}{D} = \frac{T_a}{T_i}.$$

The invention claimed is:

1. An electrosurgical generator having connectors for an electrosurgical instrument, the electrosurgical generator comprising:
   a voltage generator that is electrically connected to the connectors, the voltage generator being configured to produce an alternating current having a frequency in an activated state and output the alternating current via the connectors; and
   an effective power determination controller including:
   a phase shift determination unit configured to determine a phase shift between a current and a voltage of the alternating current output during operation, the phase shift determination unit being configured to generate a pulsed direct current (DC) voltage signal, in which a pulse width reflects a time difference between zero crossings of the current and the voltage, which consequently represents the phase shift, the phase shift determination unit being configured to process the generated pulsed DC voltage signal using a low-pass filter to form a low-pass filter output signal, a magnitude of the low-pass filter output signal is based on the pulse width of the pulsed DC voltage signal, and a switch unit configured to control the supply of the pulsed DC voltage to the low-pass filter so that the low-pass filter is only supplied with the pulsed DC voltage when the voltage generator is switched on, and not when the voltage generator is switched off.

2. The electrosurgical generator pursuant to claim 1, wherein the phase shift determination controller has a zero crossing detector that generates the pulsed DC voltage in dependence on the phase shift, and the switch unit is arranged between an output of the zero crossing detector and an input of the low-pass filter.

3. The electrosurgical generator pursuant to claim 1, wherein the switch unit is realized as an AND gate, one of the inputs of which is connected to an output of the phase shift determination controller and the other input of which receives, when the voltage generator is in the activated state, a generator-on signal, and the output of which is connected to the low-pass filter.

4. The electrosurgical generator pursuant to claim 1, wherein:

the zero crossing detector includes a first comparator and a second comparator, the first comparator being configured to compare a voltage signal with a zero signal and to produce if the low-pass filter output signal based on an instantaneous value of the voltage that is greater than the zero signal, the second comparator being configured to compare a zero signal with a current signal and to produce the low-pass filter output signal based on the zero signal being greater than an instantaneous value of the current, and outputs of the comparators are connected to each other so that the first and second comparators will only output a combined output signal as a zero crossing detector output signal with a magnitude exceeding a threshold value, when the instantaneous value of the voltage is greater than the zero signal, and when, at the same time, the instantaneous value of the current is less than the zero signal.

5. The electrosurgical generator pursuant to claim 1, wherein:

the voltage generator is configured to output, in the activated state, the alternating current pulsed with a duty cycle via the connectors, and the effective power determination controller is configured to multiply a DC voltage by a correction value $$\left(\frac{1}{D}\right)$$

dependent on the duty cycle and to output a corrected DC voltage as a signal representing the phase shift.

6. The electrosurgical generator pursuant to claim 5, wherein the correction value $$\left(\frac{1}{D}\right)$$

corresponds to a reciprocal $$\left(\frac{1}{D}\right)$$

of the duty cycle.

7. The electrosurgical generator pursuant to claim 1, further comprising a control unit that is connected to the voltage generator and controls the voltage generator during the operation.

8. The electrosurgical generator pursuant to claim 7, wherein the control unit is connected to the effective power determination controller and configured to receive the output signal from the effective power determination controller, which depends on the phase shift between the current and the voltage of the alternating current output by the electrosurgical generator during the operation.

9. The electrosurgical generator pursuant to claim 7, wherein the control unit is connected to the effective power determination controller and configured to output a signal representing a duty cycle to the effective power determination controller.

* * * * *